(12) United States Patent
Shirahama

(10) Patent No.: US 11,844,711 B2
(45) Date of Patent: Dec. 19, 2023

(54) STENT

(71) Applicant: SB-KAWASUMI LABORATORIES. INC., Kanagawa (JP)

(72) Inventor: Noriaki Shirahama, Oita (JP)

(73) Assignee: SB-KAWASUMI LABORATORIES, INC., Kanagawa (JP)

( * ) Notice: Subject to any disclaimer, the term of this patent is extended or adjusted under 35 U.S.C. 154(b) by 303 days.

(21) Appl. No.: 17/041,480

(22) PCT Filed: Mar. 20, 2019

(86) PCT No.: PCT/JP2019/011636
§ 371 (c)(1),
(2) Date: Sep. 25, 2020

(87) PCT Pub. No.: WO2019/188636
PCT Pub. Date: Oct. 3, 2019

(65) Prior Publication Data
US 2021/0121307 A1 Apr. 29, 2021

(30) Foreign Application Priority Data
Mar. 29, 2018 (JP) .................................. 2018-065755

(51) Int. Cl.
*A61F 2/88* (2006.01)
*A61F 2/07* (2013.01)
*A61F 2/915* (2013.01)

(52) U.S. Cl.
CPC .................. *A61F 2/88* (2013.01); *A61F 2/07* (2013.01); *A61F 2/915* (2013.01); *A61F 2210/0057* (2013.01)

(58) Field of Classification Search
CPC ....................................................... A61F 2/88
See application file for complete search history.

(56) References Cited

U.S. PATENT DOCUMENTS

| 6,569,191 B1 * | 5/2003 | Hogan | A61F 2/90 623/1.2 |
| 2005/0129731 A1 * | 6/2005 | Horres | A61L 31/10 514/183 |

(Continued)

FOREIGN PATENT DOCUMENTS

| JP | 2001 327609 | * 11/2001 | A61F 2/88 |
| JP | 2001-327609 | 11/2001 | |

(Continued)

OTHER PUBLICATIONS

International Search Report and the Written Opinion dated Jun. 11, 2019 From the International Searching Authority Re. Application No. PCT/JP2019/011636 and Its Translation of Search Report Into English. (9 Pages).

*Primary Examiner* — Leslie Lopez

(57) ABSTRACT

This covered stent 100, which is released from a sheath 200 and placed in a lumen in a living body, is provided with: a tubular skeleton portion 11 which is stretchable in the axial direction and is expandable in the radial direction substantially perpendicular to the axial direction; and a stretch restriction portion 2 for restricting stretching of the skeleton portion in the axial direction. The stretch restriction portion is formed from a material different from that of the skeleton portion and restricts stretching of the skeleton portion in the axial direction when the skeleton portion is contracted in the radial direction while being stored in the sheath.

10 Claims, 3 Drawing Sheets

(56) References Cited

U.S. PATENT DOCUMENTS

| | | | | |
|---|---|---|---|---|
| 2010/0004725 A1* | 1/2010 | Zipse | ............ | A61F 2/966 |
| | | | | 623/1.22 |
| 2011/0264186 A1* | 10/2011 | Berglund | ............ | A61F 2/86 |
| | | | | 623/1.11 |
| 2017/0296325 A1* | 10/2017 | Marrocco | ............ | A61F 2/88 |

FOREIGN PATENT DOCUMENTS

| | | |
|---|---|---|
| JP | 2004-517648 | 6/2004 |
| WO | WO 2019/188636 | 10/2019 |

\* cited by examiner

STENT

TECHNICAL FIELD

The present invention relates to a stent.

BACKGROUND ART

There has been a known stent that is placed in a stenosis site or an occluded site generated in a living body lumen such as blood vessel, esophagus, bile duct, and large intestine, and increases a diameter of a lesion site to maintain an opening state of the living body lumen. Also, there has been a known covered stent in which a side face of a stent main body is covered with a cover.

Such a stent is accommodated in a sheath in a contraction state where a skeleton portion contracts, and transported to a lesion (e.g. a stenosis site or an occluded site of a digestive tract, or the like), then released from the sheath, and transformed into an expansion state where the skeleton portion expands.

PRIOR ART DOCUMENT

Patent Document

Patent Document 1: Japanese Patent Laid-Open No. 2001-327609

SUMMARY OF THE INVENTION

Technical Problem

Incidentally, for example, a stent or the like having a skeleton portion around which a wire rod is spirally wound stretches in an axial direction in a contraction state where the stent is accommodated in a sheath. Thus, a contact area between an outer face portion of the stent and an inner face portion of the sheath relatively increase, and a resistance caused when the stent is released from the sheath increases. Also, when the stent is released from the sheath, the stent further stretches in the axial direction, and therefore there is also a possibility that the stent cannot be properly released from the sheath.

Furthermore, when the stent is released from the sheath and expands, an axial reduction rate (shortening) of the skeleton portion increases, which makes it difficult to accurately place the stent at a target placement site in a living body lumen.

An object of the present invention is to provide a stent that can be properly released from a sheath and an axial reduction rate can be decreased when in an expansion state.

Solution to Problem

The stent according to the present invention is
a stent that is released from a sheath and placed in a living body lumen, the stent including
a skeleton portion in a tubular form, the skeleton portion being stretchable in an axial direction and both expandable and contractable in a radial direction substantially perpendicular to the axial direction, and
a stretch restriction portion that restricts axial stretching of the skeleton portion, wherein
the stretch restriction portion is
made of a material different from the material for the skeleton portion, and restricts the axial stretching of the skeleton portion when the skeleton portion contracts in the radial direction while being accommodated in the sheath.

Advantageous Effect of the Invention

According to the present invention, a stent can be properly released from a sheath, and an axial reduction rate can be decreased when in an expansion state.

DESCRIPTION OF THE EMBODIMENT

Hereinafter, an embodiment of the present invention will be explained with reference to the figures.

Figure 1:
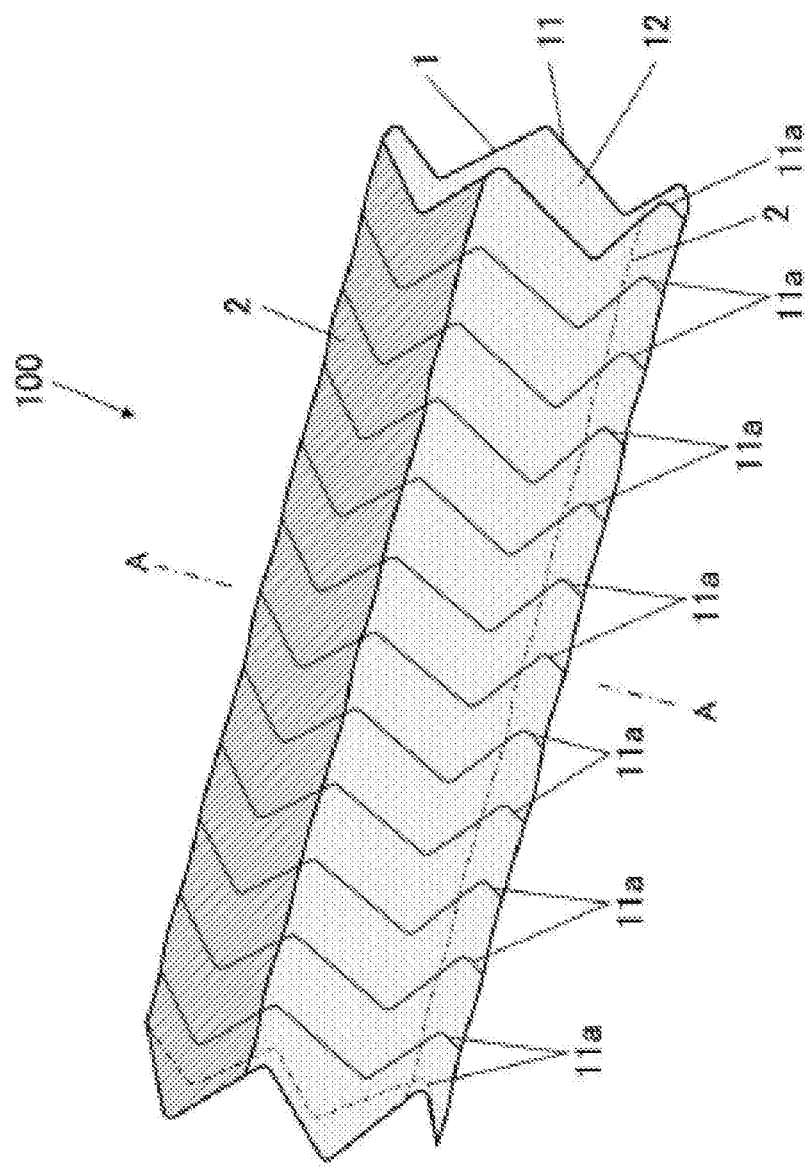
FIG. 1 is a perspective view illustrating a schematic configuration of a covered stent of an embodiment according to the present invention.
Figure 2:
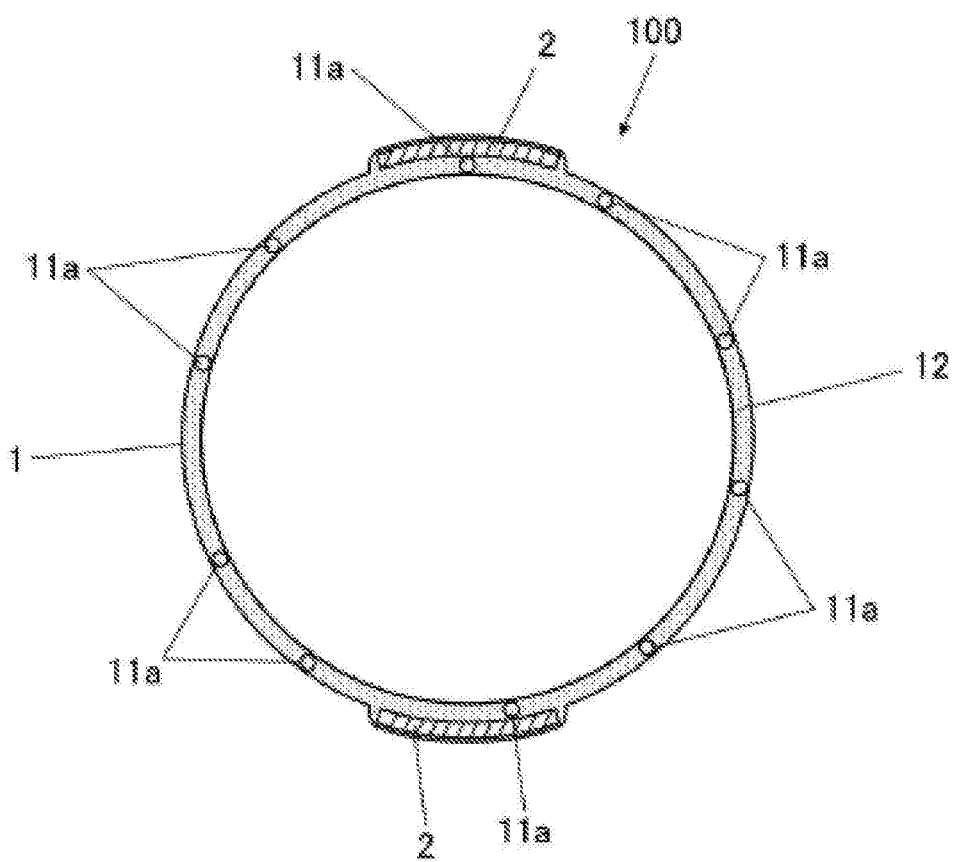
FIG. 2 is a sectional view illustrating the covered stent taken along A-A in FIG. 1.

FIG. 1 is a perspective view illustrating a schematic configuration of a covered stent 100 of an embodiment according to the present invention, and FIG. 2 is a sectional view illustrating the covered stent 100 taken along A-A in FIG. 1. Incidentally, in this embodiment, the covered stent 100 that is used while placed in a digestive tract e.g. for the purpose of treating occlusion (stenosis) by widening an occluded site (or stenosis site) in a digestive tract (e.g. large intestine; not illustrated in the figure) outward in a radial direction will be explained as an example.

As illustrated in FIG. 1, the covered stent 100 includes a stent main body portion 1, and a stretch restriction portion 2 for restricting an axial stretching of a skeleton portion 11 (described later) of this stent main body portion 1.

The stent main body portion 1 demarcates e.g. a tubular passage through which a matter flowing through the digestive tract can pass, and includes a skeleton portion 11, and a membrane portion 12 fixed so as to cover the skeleton portion 11 and the stretch restriction portion 2.

Incidentally, the matter flowing through the digestive tract includes e.g. a food immediately after intake, that has not been digested at all, a decomposed food that has passed through the digestive tract, and a matter that has not been digested even through the digestive tract (e.g. stool, or the like), and the like, regardless of a state of the matter.

The skeleton portion 11 is formed e.g. by spirally winding a thin metal wire (wire rod) 11a. Specifically, in the skeleton portion 11, for example, a thin metal wire 11a having a circular or elliptical sectional shape is spirally wound while bending such that crest portions and trough portions are alternately formed.

In addition, the skeleton portion 11 is self-expansible from a state of contracting inward in a radial direction substantially perpendicular to an axial direction to a state of expanding outward in the radial direction to demarcate a tubular passage. Specifically, for example, the skeleton portion 11 stretches in the axial direction while contracting inward in the radial direction, meanwhile shortens in the axial direction while expanding outward in the radial direction. In addition, when the skeleton portion 11 expands, an inner face of the digestive tract is pressed by an outer face of the covered stent 100. In this state, the skeleton portion 11 can be transformed depending on an external force applied from the outer face side.

In such a way, the skeleton portion 11 is formed into a tubular shape that is stretchable in the axial direction and both expandable and contractable in the radial direction substantially perpendicular to the axial direction.

Incidentally, examples of a material constituting the thin metal wire 11*a* of the skeleton portion 11 include known metals or metal alloys typified by Ni—Ti alloy (Nitinol), titanium alloy, stainless steel, and the like. In addition, for example, the material of the skeleton portion 11 (Nitinol, or the like), a sectional area and the sectional shape of the thin metal wire 11*a* (a circular wire rod such as wire, or a square wire rod formed by laser cut) of the skeleton portion 11, a number of folds and a shape of folds (a number of crest portions and a shape of crest portions) of the skeleton portion 11 in a circumferential direction, a spiral pitch of the skeleton portion 11 in the axial direction (an amount of skeletons per unit length of the covered stent 100), and the like can be set to an appropriate value suitable for being placed in a living body lumen, but their detailed explanation is omitted herein.

The membrane portion 12 is disposed on a space formed from the thin metal wire 11*a* constituting the skeleton portion 11. For example, the membrane portion 12 is fixed so as to cover the skeleton portion 11 from the outer face side, specifically fixed so as to cover the skeleton portion 11 and the stretch restriction portion 2 to demarcate the aforementioned tubular passage. Herein, the membrane portion 12 may cover the skeleton portion 11 so as to sandwich the skeleton portion 11 from the outer face side and the inner face side, or may cover the skeleton portion 11 only from the outer face side, or may cover the skeleton portion 11 only from the inner face side. Incidentally, examples of the material for the membrane portion 12 include a silicon resin, a fluorine resin such as polytetrafluoroethylene (PTFE), a polyester resin such as polyethylene terephthalate, and the like.

The stretch restriction portion 2 is disposed along the axial direction of the skeleton portion 11. For example, the stretch restriction portion 2 is a long member fixed (e.g. by adhesion, or the like) to the outer face side of the skeleton portion 11 over both ends in the axial direction of the skeleton portion 11, in which a width substantially perpendicular to the axial direction is substantially constant. In addition, two stretch restriction portions 2 are disposed e.g. with a predetermined interval (e.g. 180° interval) in the circumferential direction.

In addition, the stretch restriction portion 2 is made of a material different from that of the skeleton portion 11. Specifically, the stretch restriction portion 2 is made of at least one of a biocompatible thread (e.g. polyester thread, or the like) and a cloth (woven fabric (textile), and knitted fabric), but these cases are merely examples, and the present invention is not limited to these cases. That means, it is preferable that the stretch restriction portion 2 has at least a strength sufficient for restricting the axial stretching of the skeleton portion 11, and further has a strength that does not impair the expansibility/contractility of the covered stent 100 in the radial direction.

The covered stent 100 configured described above is accommodated in the sheath 200 (see FIG. 3B) in a contraction state where the skeleton portion 11 contracts, and for example, the covered stent 100 is transported to a stenosis site or an occluded site of a digestive tract, then released from the sheath 200, and transformed into an expansion state where the skeleton portion 11 expands.

Next, a state of the covered stent 100 accommodated in the sheath 200 will be explained with reference to FIG. 3A to FIG. 3C.

Figure 3A:
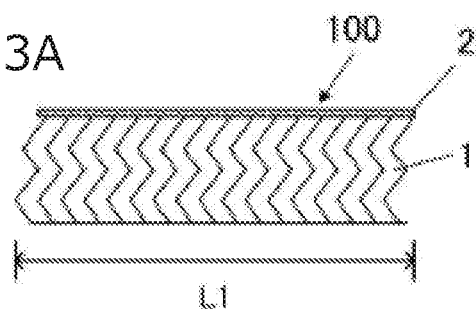
FIG. 3A is a diagram for explaining a state of the accommodated covered stent in FIG. 1.
Figure 3B:
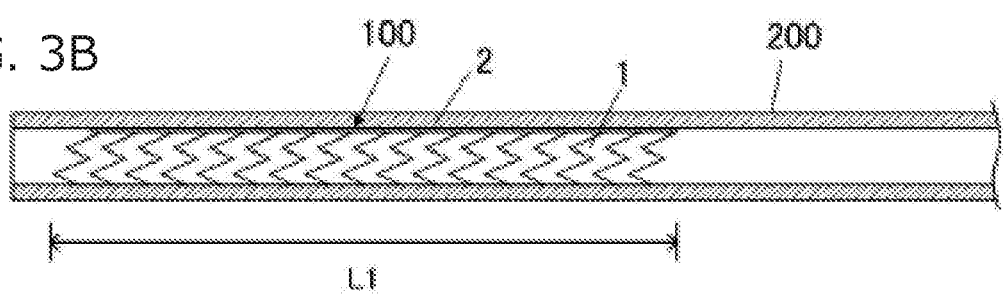
FIG. 3B is a diagram for explaining a state of the accommodated covered stent in FIG. 1.
Figure 3C:
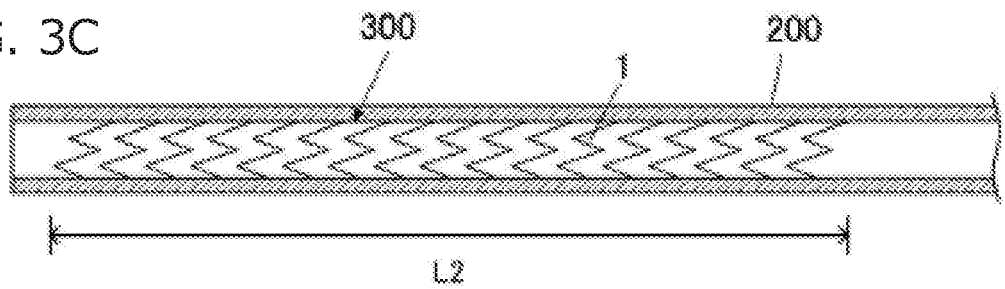
FIG. 3C is a diagram for explaining a state of the accommodated covered stent in FIG. 1.

FIG. 3A is a schematic diagram illustrating the covered stent 100, and FIG. 3B is a schematic diagram illustrating a state where the covered stent 100 is accommodated in the sheath 200. In addition, FIG. 3C is a schematic diagram illustrating a state where a stent 300 without the stretch restriction portion 2 is accommodated in the sheath 200.

As illustrated in FIG. 3A and FIG. 3B, the covered stent 100 contracts inward in the radial direction and stretches in the axial direction when accommodated in the sheath 200. Herein, since the covered stent 100 includes the stretch restriction portion 2, the axial stretching of the skeleton portion 11 is restricted by this stretch restriction portion 2. That means, when the covered stent 100 including the stretch restriction portion 2 is accommodated in the sheath 200, a length L1 in the axial direction of the stent 100 increases, but the length L1 in the axial direction is smaller than an length L2 in the axial direction of the stent 300 without the stretch restriction portion 2 when similarly accommodated in the sheath 200 (see FIG. 3B and FIG. 3C).

As described above, the covered stent 100 according to this embodiment is released from the sheath 200 and placed in a living body lumen (e.g. digestive tract, or the like), and includes the tubular skeleton portion 11 stretchable in the axial direction and both expandable and contractable in the radial direction substantially perpendicular to the axial direction, and the stretch restriction portion 2 (e.g. biocompatible thread, cloth, or the like) for restricting the axial stretching of the skeleton portion 11. The stretch restriction portion 2 is made of a material different from that of the skeleton portion 11, and configured to restrict the axial stretching of the skeleton portion 11 when the skeleton portion 11 contracts in the radial direction while being accommodated in the sheath 200.

Thus, even if the skeleton portion 11 contracts in the radial direction when the covered stent 100 is accommodated in the sheath 200, the covered stent 100 is accommodated in the sheath 200 while the stretching in the axial direction of the skeleton portion 11 is restricted by the stretch restriction portion 2. That means, compared to the stent 300 without the stretch restriction portion 2, the length L1 in the axial direction of the covered stent 100 can be relatively decreased, and a contact area between the outer face portion of the covered stent 100 and the inner face portion of the sheath 200 can be relatively decreased, so that a resistance caused when the stent 100 is released from the sheath 200 can be decreased. Thereby, the covered stent 100 can be properly released from the sheath 200.

Furthermore, since the length L1 in the axial direction of the covered stent 100 accommodated in the sheath 200 can be relatively decreased, a reduction rate in the axial direction of the expanded skeleton portion 11 can be decreased when the covered stent 100 is released, so that the covered stent 100 can be desirably placed on a target placement site in a living body lumen such as digestive tract.

In addition, for example, when the covered stent 100 accommodated in the sheath 200 is released from the sheath 200, even if the covered stent 100 is displaced in the axial direction relative to the sheath 200, the stretch restriction portion 2 restricts the stretching of the skeleton portion 11 in the axial direction. That means, for example, when the covered stent 100 is released by drawing the sheath 200 toward the proximal side with respect to the covered stent 100, there is a possibility that the covered stent 100 further stretches in the axial direction and the resistance caused during release increases, depending on a frictional resistance between the inner face portion of the sheath 200 and the outer face portion of the covered stent 100. At this time, the axial stretching of the skeleton portion 11 is restricted by the stretch restriction portion 2 to suppress further stretching of the covered stent 100 in the axial direction, so that the resistance caused during release can be further decreased.

As described above, the invention made by the present inventors has been specifically explained on the basis of the embodiment, but the present invention is not limited to the above embodiment, and can be modified without departing from the gist of the present invention.

For example, in the above embodiment, the covered stent 100 having the membrane portion 12 has been described as an example, but is merely an example, and the present invention is not limited to this embodiment. Disposition of the membrane portion 12 is optional. That means, although not illustrated in the figure, the stent according to the present invention may be configured such that the skeleton portion 11 is not covered by the membrane portion 12 (bare stent).

Additionally, in the above embodiment, the membrane portion 12 disposed so as to cover the stretch restriction portion 2 has been described as an example, but is merely an example, and the present invention is not limited to this embodiment. For example, the stretch restriction portion 2 may be disposed outside the membrane portion 12. According to such a configuration, the covered stent 100 is placed such that a tube wall of the living body lumen and the stretch restriction portion 2 are in contact with each other, so that cells on the tube wall can make inroads into the stretch restriction portion 2. Thereby, the stretch restriction portion 2 can function as a restriction means for preventing the covered stent 100 from deviating from the placement position.

Furthermore, in the above embodiment, the stretch restriction portion 2 made of cloth has been described as an example, but is merely an example, and the present invention is not limited to this embodiment. For example, the stretch restriction portion 2 may be made of the same material as of the membrane portion 12. That means, the thickness of the membrane portion 12 is partially uneven, and a part thicker than of the other part may function as a stretch restriction portion. Even in such a configuration, the axial stretching of the skeleton portion 11 can be properly restricted when the covered stent 100 is accommodated in the sheath 200 and the skeleton portion 11 contracts in the radial direction, so that the covered stent 100 can be properly released from the sheath 200, and the reduction rate in the axial direction can be decreased when in an expansion state.

In addition, in the above embodiment, the stretch restriction portion 2 disposed on the outer face side of the skeleton portion 11 has been described as an example, but is merely an example, and the present invention is not limited to this embodiment. For example, the stretch restriction portion 2 may be disposed on the inner face side of the skeleton portion 11 or on both the outer face side and the inner face side of the skeleton portion 11.

Furthermore, the skeleton portion 11 may be formed e.g. by laser processing (laser cut) of one metal pipe (e.g. pipe made of Ni—Ti alloy, or the like).

In addition, in the above embodiment, the covered stent 100 to be used while placed in the digestive tract has been described as an example, but is merely an example, and the present invention is not limited to this embodiment. For example, the stent may be placed in a living body lumen other than the digestive system lumen, a blood vessel, or the like.

Note that the embodiment disclosed in this specification should be regarded as an example in all regards and considered to be unrestrictive. The scope of the present invention is stipulated not by the aforementioned explanation but by claims, and intended to include meanings equivalent to claims, and all modifications within the scope of claims.

Disclosure contents of specifications, figures, and abstracts included in Japanese Patent Application No. 2018-065755 filed on Mar. 29, 2018 are all incorporated in this application.

DESCRIPTION OF REFERENCE NUMERALS

100 Covered stent
1 Stent main body portion
11 Skeleton portion
11a Thin metal wire (wire rod)
12 Membrane portion
2 Stretch restriction portion
200 Sheath

What is claimed is:

1. A stent that is released from a sheath and placed in a living body lumen, the stent comprising:
   a skeleton portion in a tubular form, the skeleton portion being stretchable in an axial direction and both expandable and contractable in a radial direction substantially perpendicular to the axial direction;
   a stretch restriction portion that restricts axial stretching of the skeleton portion; and
   a membrane portion that is disposed so as to cover at least an entire outer surface of the skeleton portion, wherein
   the stretch restriction portion is an axial member made of a first material different from a second material for the skeleton portion and having a width in a circumferential direction that is less than a circumference of the stent, the width being equal over the entire length of the stretch restriction portion, and the stretch restriction portion is disposed along the axial direction in the membrane portion, and
   a portion of the stent in which the stretch restriction portion is disposed protrudes radially outwardly relative to a portion in which the stretch restriction portion is not disposed.

2. The stent according to claim 1, wherein
   the stretch restriction portion restricts the axial stretching of the skeleton portion when the stent accommodated in the sheath is axially displaced relative to the sheath.

3. The stent according to claim 1, wherein
   the skeleton portion is formed of at least one metal wire rod having a circular or elliptical sectional shape wound in a spiral shape while bending such that crest portion and trough portion are alternately formed in the axial direction.

4. The stent according to claim 3, wherein
   the membrane portion constitutes a stent main body together with the skeleton portion and is disposed in a space formed by the metal wire rod of the skeleton portion.

5. The stent according to claim 3, wherein
   the membrane portion covers the skeleton portion so as to sandwich the skeleton portion from an outer face side and an inner face side.

6. The stent according to claim 3, wherein
a plurality of the crest portions form at least one group of crest portions disposed in a straight line in the axial direction,
a plurality of the trough portions form at least two groups of trough portions disposed in a straight line in the axial direction and flanking the group of crest portions in a circumferential direction,
the stretch restriction portion is disposed along the axial direction so as to cover a portion from the group of crest portions to a vicinity of the two group of trough portions.

7. The stent according to claim 1, wherein
the stretch restriction portion is covered by the membrane portion.

8. The stent according to claim 1, wherein
the stretch restriction portion is disposed on an outer surface of the membrane portion and is exposed from the outer surface of the membrane portion.

9. The stent according to claim 1, wherein
the stretch restriction portion is fixed over both ends of the skeleton portion in the axial direction.

10. The stent according to claim 1, wherein
the stretch restriction portion includes two members disposed with a 180° interval in a circumferential direction.

\* \* \* \* \*